(12) United States Patent
Gervasio

(10) Patent No.: US 8,470,350 B2
(45) Date of Patent: Jun. 25, 2013

(54) COSMETIC COMPOSITIONS AND CONTAINER THEREFOR

(76) Inventor: Carla Gervasio, New York, NY (US)

( * ) Notice: Subject to any disclaimer, the term of this patent is extended or adjusted under 35 U.S.C. 154(b) by 0 days.

(21) Appl. No.: 12/833,208

(22) Filed: Jul. 9, 2010

(65) Prior Publication Data

US 2011/0081372 A1 Apr. 7, 2011

Related U.S. Application Data

(60) Continuation of application No. 11/373,731, filed on Mar. 10, 2006, now abandoned, which is a division of application No. 10/165,369, filed on Jun. 7, 2002, now abandoned.

(51) Int. Cl.
*A61K 8/02* (2006.01)
*A61K 36/00* (2006.01)
*A01N 65/00* (2009.01)

(52) U.S. Cl.
USPC .......................................... 424/401; 424/725

(58) Field of Classification Search
USPC ....................................................... 424/401
See application file for complete search history.

(56) References Cited

U.S. PATENT DOCUMENTS 5,916,573 A * 6/1999 Spiers et al. .................. 424/401

FOREIGN PATENT DOCUMENTS

EP 923938 A1 * 6/1999
EP 1192938 A2 * 4/2002

OTHER PUBLICATIONS

Dweck et al. (Natural Extracts and Herbal oils Concentrated Benefits for the Skin).*
Miczak. (Secret potions, elixirs & concoctions: botanical & aromatic recipes for mind, body & soul. 1999).*
Bakhru (Indian Spices & Condiments As Natural Healers. 2001).*
Dweck et al. (Natural Extracts and Herbal oils Concentrated Benefits for the Skin. Cosmetics and Toiletries. vol. 107 May 1992).*

* cited by examiner

*Primary Examiner* — Sreeni Padmanabhan
*Assistant Examiner* — Layla Soroush
(74) *Attorney, Agent, or Firm* — Louis C. Paul

(57) ABSTRACT

A self-standing container holds particles of a cosmetic composition. The container may be cup-shaped or box-shaped, for example, and made of laminated paper or polystyrene. When ready to use, the user opens the container and adds liquid or gel to mix with the dry particles to form a moist cosmetic composition, so no separate mixing container or measuring cup is necessary. The composition formed is suitable for treating a user's skin and/or hair. A fill mark on the container informs the user of a proper amount of the liquid or gel to add to the container. The particles may include both ground-up and whole particles from substances such as dried botanicals (plant ingredients) and a binding agent. A cosmetic composition includes a ready-to-mix mixture of ingredients including particles from dried herbs and/or flowers and a dried food, and an essential oil.

4 Claims, 4 Drawing Sheets

COSMETIC COMPOSITIONS AND CONTAINER THEREFOR

CROSS REFERENCE TO RELATED APPLICATIONS

The present application is a continuation of U.S. Ser. No. 11/373,731, filed Mar. 10, 2006 now abandoned, which is a division of U.S. Ser. No. 10/165,369, filed Jun. 7, 2002 now abandoned, the contents of each of which is fully incorporated herein by reference.

BACKGROUND OF THE INVENTION

The present invention provides cosmetic compositions and a container therefor that allow a user to easily prepare and dispense a treatment for the skin or hair.

A huge market exists in cosmetic compositions, including skin and hair care treatments. Such treatments may be applied to the face or other skin areas, or the hair, to produce a cleansing, purifying, relaxing effect. Ready-to-use compositions in the form of skin creams, body lotions, or facial masks are currently available, for example, in a jar or tube. As an example, U.S. Pat. No. 4,569,839 describes a cosmetic composition of this type. In this case, the user need only open the jar or tube and apply the composition to the skin with their fingers, a towel, or other applicator. Also, dry powder mixes are currently commercially available that can be mixed immediately prior to use with a liquid or gel to form a moist composition that can then be applied to the skin. In this case, the dry powder mix is emptied from its container into a bowl or other container, then liquid or gel is added to and mixed with the powder mix.

The present invention provides cosmetic compositions and a container therefor that provides improved convenience.

SUMMARY OF THE INVENTION

The present invention provides cosmetic compositions and a container that enables users to quickly and conveniently mix an instant, fresh batch of a cosmetic composition in their homes or other location. The invention enables preparation of a cosmetic composition that has an optimal consistency each time it is used, thereby avoiding waste and less-than-optimal performance.

Among other things, the invention addresses the consumer's demand for products that provide immediate results, while being convenient and even fun to use, and the consumer's preference for products that incorporate natural ingredients, including flowers, and other botanicals.

In particular, a cosmetic composition and container therefor according to the invention includes a self-standing container that is nominally closed, but can be opened by a user when ready to use. The container is constructed to at least temporarily hold a liquid or gel added thereto when the container is opened. For example, the container may be cup-shaped and constructed from paper, Styrofoam or other disposable material. The composition includes particles made from selected ingredients for forming a cosmetic composition with a desired consistency when mixed with a suitable liquid or gel. The particles are sealed within the container. For example, the particles may be loose or bulk within and sealed by the container, or the particles may be sealed within a separate sealed container or package within a larger container in which the mixing is carried out. The mixed composition formed in the container is suitable for treating a user's skin and/or hair, e.g., as a scrub, mask or cleanser, or a shampoo or rinse treatment.

The particles may include both ground-up and whole particles from substances such as dried botanicals (plant ingredients), including dried foods, herbs, florals (flowers) and cereals/grains, and a binding agent such as wheat, rice, flour, oats, clay and iron oxides. The binding agent causes the particles to form a thickened composition. Moreover, a botanical such as oat bran flour can also serve as a binding agent in which case a separate binding agent may not be needed.

In one embodiment, the container has a fill mark that informs the user of a proper amount of the liquid or gel to add to the container to form the cosmetic composition with a desired consistency.

In one embodiment, a package may be carried within the container that holds the liquid or gel that is to be mixed with the particles to form the cosmetic composition with a desired consistency. In this way, a self-contained kit is provided. A stirring spoon, stick or other implement may also be packaged with the container.

A method for packaging and using a cosmetic composition includes providing particles comprising selected ingredients for treating a user's skin and/or hair in a container, and closing the container, such as by sealing it with a lid. The container is a self-standing, closed, openable container that is constructed to at least temporarily hold a liquid or gel added thereto when the container is opened. The method also includes opening the container, when ready to use by a user, and mixing in a suitable liquid or gel to form a cosmetic composition for treating a user's skin and/or hair.

A cosmetic composition includes a ready-to-mix mixture of ingredients including particles made from dried herbs and/or flowers, particles made from a dried food, and one or more types of essential oil, either in particle or liquid form.

DETAILED DESCRIPTION OF PREFERRED EMBODIMENTS

Figure 1:
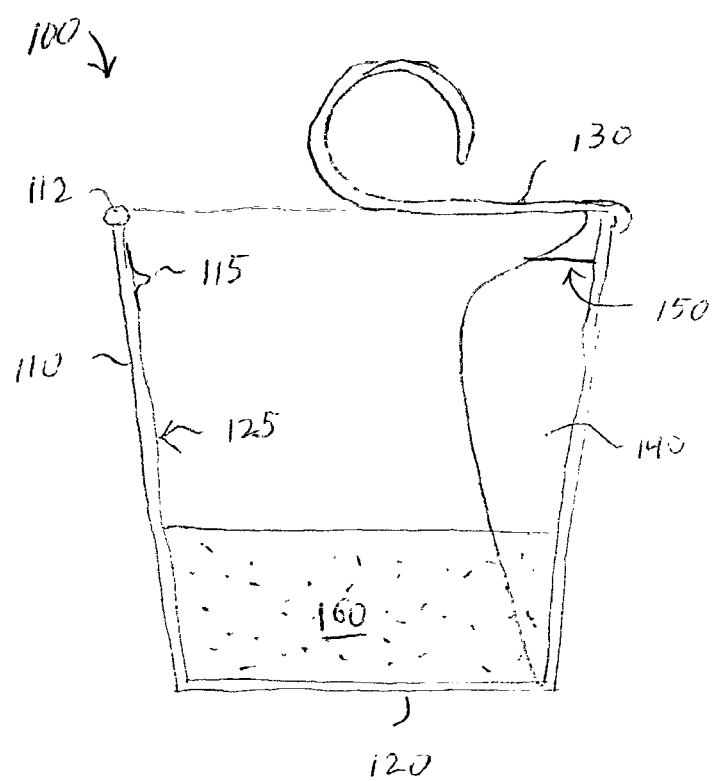
FIG. 1 illustrates a cosmetic composition and container, with a lid in a partially opened position, and with an outer surface of the container shown in a partial cutaway view.

FIG. 1 illustrates a cosmetic composition and container, with a lid in a partially opened position, and with an outer surface of the container shown in a partial cutaway view. The container, shown, generally at 100, is cup-shaped in this embodiment, although other shapes are possible. The container 100 includes a wall portion 110 and a bottom portion 120 that enables the container to be self-standing, e.g., to stand up by itself when placed on a flat surface such as a table or countertop. The wall portion 110 and bottom portion 120 may be made of paper, plastic, Styrofoam/polystyrene or other suitable material. Optionally, the container may be made of a transparent material, or a heavier material such as glass, metal, porcelain or ceramic. The outer face of the wall portion may have printing directly on it, or a label 140 with printing on it may be adhered to the outer face. The printing may indicate the ingredients of the particles 160, as well as providing directions for use. Example directions may read as follows:

Directions:

Fold lid halfway back; add water to FILL LINE on outside of cup.

Stir very well to bring all ingredients up from the bottom. Remove lid.

Let stand for 5 minutes.

Stir again and apply.

In a facial mask application, the user may also be directed as follows:

For an extra rich and soothing mask, substitute warm water with warm whole milk or cream.

Apply to face in circular motion and leave on for ten minutes.

Wash off with warm or cool water.

The user may also be warned that the product is for external use only and is not to be consumed. Additionally, graphical instructions may be provided, e.g., which show a liquid being poured into the cup with the lid half open, a user stirring the composition with the lid off, and the composition applied to a user's face. The user may further be instructed to apply the composition to the skin with their fingers, a towel, or other applicator, e.g., as a topical application.

Optionally, the user may be directed to heat up the mixture in a microwave oven for a given period of time. The fill line mentioned above may be printed on the outer face and/or inner face of the wall portion 100, e.g., as shown by fill line mark 150. Moreover, a fill line may be indicated by a protrusion or similar mark 115. The fill mark 115, 150 informs the user of a proper amount of the liquid or gel to add to the container to form the cosmetic composition with a desired, optimal consistency. Thus, the user can obtain good results reliably without the need for measuring cups or the like. The location of the fill mark 115, 150 is determined based on the volume displaced in the container by the particles and corresponding liquid or gel. Moreover, multiple fill marks may be provided at different heights along the container when there are multiple possible formulations. For example, the different fill marks may reflect the fact that different optimal amounts are used for a liquid versus a gel, or for different types of liquids (e.g., water versus milk or fruit juice). As an example, less milk may be used than water since milk is thicker, so the fill mark for milk might be lower than for water.

An inner face 125 of the wall portion 110 may be coated/laminated with a liquid-resistant material such as wax, plastic or foil to prevent liquid from penetrating the wall portion 110.

The container 100 further includes a lid or cover 130 that may have various configurations. In one possibility, the lid 130 is a pliable material, such as paper with a plastic or foil sheeting, that is adhered to a circumferential lip 112 of the container 100. Another possibility is to use a twist off cap.

Generally, the container 100 may be fabricated using known technologies, such as discussed in U.S. Pat. No. 4,094, 996, entitled "Package of convenience food," incorporated herein by reference. This type of container is used in the "Cup of Noodles®" product of Nissin Foods, Japan. The container is preferably sized for a single use, and made of an inexpensive material so it can be discarded. The container should thus be sized to hold the desired amount of cosmetic composition particles and the corresponding amount of liquid or gel which, when mixed, form the composition. The size should also be generous enough to allow vigorous mixing by the user without excessive spillage over the container's edge. The container 100, as well as the other containers described herein, may further be packaged in an outer layer of cellophane or the like to protect the container.

The particles 160 are inserted into the container 100 prior to the lid 130 being sealed, at the time of production. Once sealed, the container 100 provides a convenient package which can be easily shipped and stored, and has a relatively long shelf life. Additionally, once purchased, the container can be easily transported by the user in a handbag, backpack or the like.

In a further possibility, the particles may be carried in a separate container or package, such as a paper, plastic or foil sachet or bag, within the container 100. In this case, the user opens the sachet and empties the particles into the container 100 before use.

The particles 160 include ingredients of a cosmetic composition. Moreover, when a suitable liquid or gel is mixed in with the particles, a cosmetic composition is formed that is useful for treating a user's skin and/or hair. For example, the particles may include both ground-up and whole particles from substances such as dried botanicals (plant ingredients), including dried foods, herbs, florals and cereals/grains, and a binding agent such as wheat, rice, flour, oats, clay and iron oxides. The binding agent enables the mixture of the particles and the liquid or gel to form a desired consistency when mixed by the user using a utensil or other appropriate implement. Generally, the consistency should be thick enough so that the mixture is not runny, yet thin enough so that it can be applied smoothly. The particles may be obtained by pulverizing the raw ingredients in a known manner. For example, grinding or micronization may be used, optionally followed by a sieving operation. Note also that the particles 160 may be in various conditions in the container, e.g., loose, clumped together, bound together, and so forth.

The particle ingredients and size may be selected based on the desired application. The beneficial properties of various plants (including shrubs, trees and portions such as roots, stems, leaves, flower, fruits and seeds) are known in the art. These properties include: emollient, anti-inflammatory, anti-pruriginous, antiseptic, antiperspirant, astringent, soothing, cicatrisive, and tonic properties. For example, see, e.g., U.S. Pat. No. 4,569,839, incorporated herein by reference. Moreover, the particle size can be tailored for the desired application. For instance, a facial mask generally benefits from a smoother texture, so smaller particles may be used. A scrub, on the other hand, preferably has a coarser texture, which can be achieved by using larger particles, including whole, ungrounded particles and coarsely-grounded particles. Generally, the composition should have a viscosity, which can range from relatively low to relatively high, which enables the composition to be easily used for its intended purpose. For example, the viscosity or consistency of a facial mask should be thick enough so it is easy to apply to the face and remains on the face without being runny. On the other hand, a relatively low viscosity or thickness, similar to a shampoo, may be desirable for a composition that is applied to the hair. The viscosity can be increased or decreased as desired, e.g., so that the composition can be applied to the hair, body, etc. with optimal ease.

Essentially, when mixed with the liquid or gel, the particles undergo a phase change from a dry or solid phase to a semi-liquid or semi-solid phase. The liquid or gel hydrates the dehydrated particles to form a moist composition.

Particle size or range of sizes will be known to those skilled in the art from the disclosure herein and a knowledge of, and experience with, ingredients of the type disclosed herein. The size of the particles may vary depending on factors such as the coarseness and consistency desired for a particular application of the mixed product, the nature and/or characteristics of the dried botanicals, the binding agent(s) used and the liquid or gel used. Suitable ranges of particle sizes will be known to those of skill in the art.

Example formulations and application for cosmetic compositions are as follows. The relative amount of each ingredient is given by volume, and can be selected as desired within any range. For example, the relative amounts of the ingredients can be increased or decreased to provide more or less of the desired quality of the ingredient. In formulation (1), for instance, to provide relatively greater soothing qualities, relatively more Chamomile flower and lavender flower can be used, e.g., 6 parts of each can be used instead of 3 parts. Moreover, note that the same ingredient can have many functions in one or more formulas. For example, ascorbic acid, which is in Vitamin C, can function as both an anti-oxidant and a preservative in the same or different formulas.

1. Nourishment scrub mask (for dry sensitive skin)
5 parts powdered soy milk, 1 part oat flour (to help hydrate)
3 parts Chamomile flower, 3 parts lavender flower (to soothe)
1 part Almond powder or 0.5 ounce sachet of Almond oil (to soften and condition)
2. Wellness scrub mask (for normal, combination skin)
1 part Ginger powder (to stimulate circulation)
0.5 ounce Grape seed oil (to hydrate and soften)
3 parts Oatmeal flour (to gently cleanse and exfoliate)
1 part *Geranium* flowers (to calm and balance)
2 parts Violet flowers (to soothe)
5 parts Powdered soy milk
3 parts clay (cleanses)
3 Wellness scrub mask 2 (for normal, combination skin)
1 part Ginger powder (to stimulate circulation)
1 part Black currant (rejuvenates tired skin, has anti-oxidant properties)
1 part Violet flower (to soothe)
0.5 ounce *Geranium* oil (to calm and balance)
3 parts Kaolin clay (helps remove impurities, detoxify skin)
3 parts Oatmeal (to gently cleanse and exfoliate)
0.5 ounce Almond oil (moisturizes, hydrates)
4. Clarify scrub mask (for acne-prone skin)
5 parts Green clay (to deep cleanse and purify)
0.25-ounce Tea tree oil or juniper oil (to combat blemishes)
1 part Marigold flower and eucalyptus (to calm irritation)
1 part Cucumber (to tone and fresh)
2 parts powdered yeast (antioxidant, soothes)
1 part Eucalyptus (has anti-bacterial properties)
5. Detox mask (for oil prone skin)
5 parts Green clay (to draw out impurities)
2 parts Seaweed (to tone and condition)
1 part Witch hazel and 1 part lemongrass (to tighten pores)
1 part chopped Apple (to gently exfoliate)
6. Detox mask 2 (for oil prone skin)
2 parts Pineapple (exfoliates)
2-5 parts clay (deep cleanses and exfoliates)
2 parts Marigold flower (has antiseptic properties)
1 part chopped Apple (clarifies)

Example ingredients for the liquid or gel include: Water, milk, beer, tomato sauce, fruit juice (e.g., apple, lemon), eggs, honey, yogurt, cucumber gel, aloe vera gel. As an example, approximately 0.25 to 0.5 cup of the liquid or gel may be added to the other ingredients, which may also comprise a volume of approximately 0.25 to 0.5 cup. Cosmetically acceptable dyes and pigments may also be used.

Generally, the cosmetic composition may include a ready-to-mix mixture of ingredients such as particles made from dried herbs and/or flowers, particles made from a dried food, and one or more essential oils, either in particle or liquid form. For example, the dried food may include a starchy food such as wheat, rice, flour and/or oats which acts as a binding agent in the mixture when a liquid or gel is mixed in with the mixture. The essential oil may be of various types, including almond, grape seed, geranium, tea tree and juniper oil. Again, these are only examples, and many other foods and oils may be used.

Note that, for a scrub application in particular, it is desirable to have an abrasive agent. This may be achieved using a natural product, such as coarsely-grounded clay, oatmeal or sand, or an artificial product such as a polymer or synthetic, e.g., such as Jojoba beads.

The examples given are meant to be illustrative rather than limiting, as the invention may use any known ingredients for forming a cosmetic composition.

Figure 2:
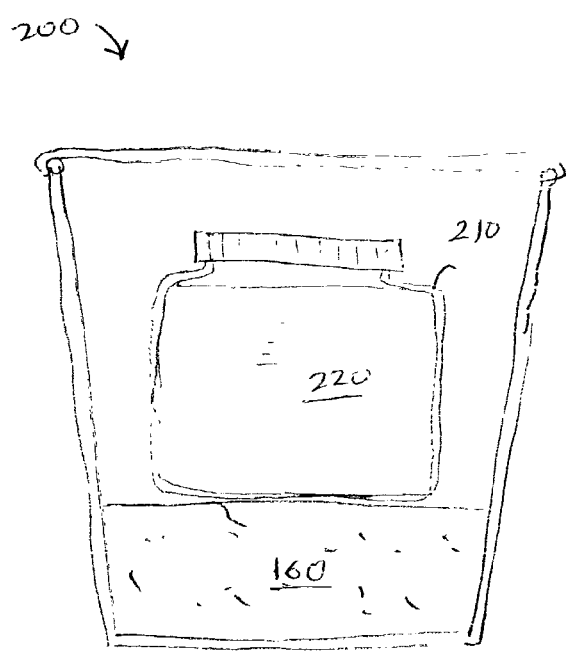
FIG. 2 illustrates a cosmetic composition and container, with a package of liquid or gel carried therein.

FIG. 2 illustrates a cosmetic composition and container, with a package of liquid or gel carried therein. Here, the container 200 includes a package 210 carried within the container that contains the liquid or gel 220 that is to be mixed with the particles 160. Preferably, the package 210 contains an optimal amount of liquid or gel for forming the composition with a desired consistency. The package may be formed of a generally rigid material such as plastic, for example, with a screw off or pull off top. Alternatively, the package may be formed of a pliable material, such as a paper, plastic or foil plastic bag, pouch, sachet, or envelope, which can be torn open to release the liquid or gel. Similarly, a vial can be used to hold the liquid or gel. Furthermore, the package 210 may be unsecured within the container 200, or secured, e.g., to the inner side wall of the container 200 using a releasable adhesive. To use, the user removes the lid from the container, then removes the package 210 and empties its contents into the container 200 to mix with the particles 160. Optionally, the package 210 may be secured to the outside of the container 200, or carried with the container 200 in another, larger container such as a paperboard box or the like.

Figure 3:
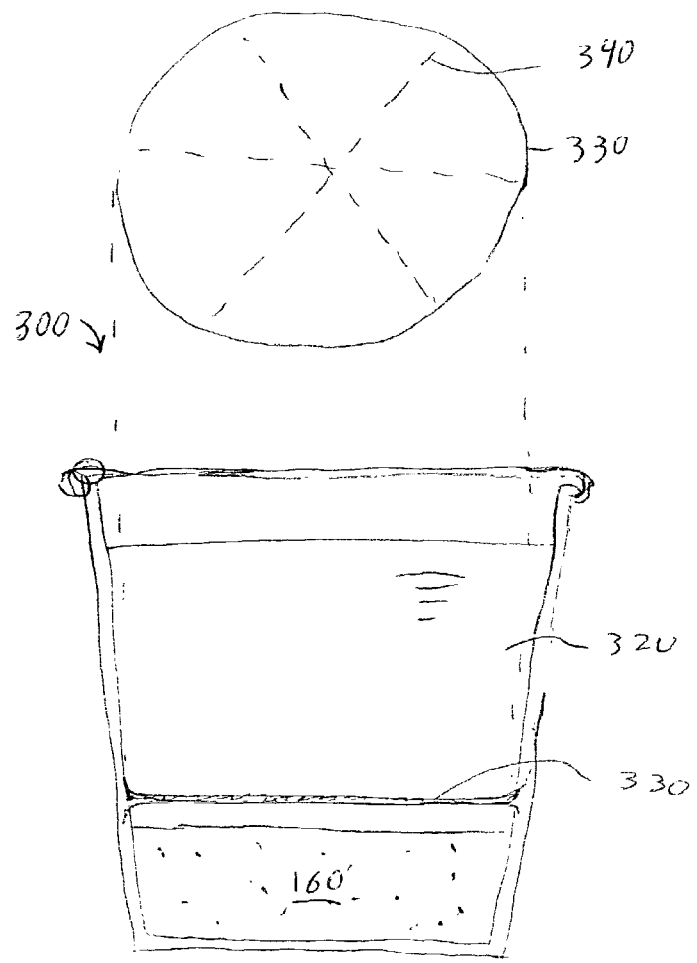
FIG. 3 illustrates a cosmetic composition and container, with a liquid or gel carried therein.

FIG. 3 illustrates a cosmetic composition and container, with a liquid or gel carried therein. Here, the liquid or gel 320 is separated from the particles by a membrane or panel 330, which may be made of foil or laminated paper, for example. In use, the user removes the cover of the container 300 and pierces the membrane 330 using a suitable implement such as a stirring stick to allow the liquid or gel to mix with the particles 160. Preferably, the membrane remains attached to the container 300 even after it is ruptured to avoid having pieces of it being mixed in with the cosmetic composition. To this end, the membrane 330 may be ruptured along diametrical score marks 340, while a circumferential or peripheral portion of the membrane 330 remains attached to the inner wall of the container 300.

Alternatively, the membrane 330 may be substantially rigid so that it can be easily pulled out of the container 300. In this case, the membrane may be weakened at its periphery so it can be pulled away from the interior wall 300 of the container by the user. To this end, the membrane may have a tether and pull ring that extends to the top of the container to be pulled by the user. In this manner, the membrane 330 can be removed from the container 300 altogether. Furthermore, the container 300 may have a step increase in its diameter that forms a seat or shoulder upon which the membrane 330 rests before it is removed by the user.

Advantageously, the embodiments of FIGS. 2 and 3 are self-contained and are ready to use without providing additional equipment or supplies.

Figure 4:
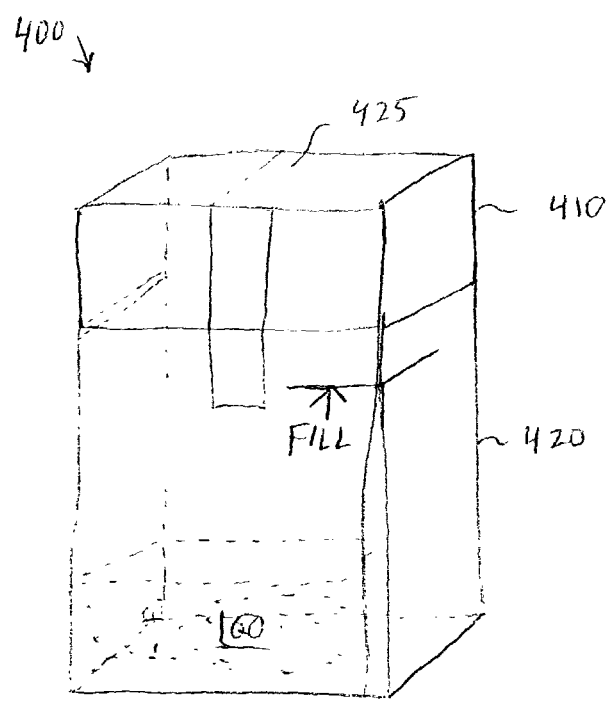
FIG. 4 illustrates a further cosmetic composition and container.

FIG. 4 illustrates a further cosmetic composition and container. The container 400 is generally box-shaped, and has a top portion 410 that may engage a bottom portion 420, or may be attached to the bottom portion 420 in a hinged manner, for instance. A seal 425, such as a ribbon with adhesive, may be provided that is broken to open the container 400. The container may be made of paperboard that is laminated on the interior, at least in the bottom portion 420, to prevent the liquid or gel from leaking through. A fill mark is included to inform the user of the appropriate amount of liquid or gel to add. Optionally, as discussed also in connection with the package 210 of FIG. 2, a package holding a liquid or gel may be carried within the container 400. In a further option, the particles 160 are carried in a separate container within the container 400

Moreover, while the container 400 is four-sided, various other container shapes may be used as well, e.g., such as containers having more than four sides, containers having both flat and rounded portions, and so forth. Additionally, the container may have a novelty shape, such as that of a house, teddy bear, doll, apple, cartoon character, or other pleasing object. Plastic forming techniques may be used to form such shapes.

Accordingly, it can be seen that the present invention provides a cosmetic composition and container therefor which includes a self-standing container that is nominally closed, but can be opened by a user when ready to use. The container is constructed to at least temporarily hold a liquid or gel added thereto when the container is opened. The composition, which is suitable for treating a user's skin and/or hair, includes particles made from selected ingredients for forming a cosmetic composition when mixed with a suitable liquid or gel. The particles may include both ground-up and whole particles from substances such as dried botanicals (plant ingredients), including dried foods, herbs, florals and cereals/grains, and a binding agent such as wheat, rice, flour, oats, clay and iron oxides. Moreover, a botanical such as oat bran flour can also serve as a binding agent in which case a separate binding agent may not be needed. Furthermore, the container may have a fill mark that informs the user of a proper amount of the liquid or gel to add to the container to form the cosmetic composition with a desired consistency. Optionally, a package may be carried within the container that holds the liquid or gel that is to be mixed with the particles to form the cosmetic composition. The particles may also be carried in a separate package within the container. A cosmetic composition includes a ready-to-mix mixture of ingredients including particles from dried herbs and/or flowers and a dried food, and an essential oil.

While the invention has been described and illustrated in connection with preferred embodiments, many variations and modifications as will be evident to those skilled in this art may be made without departing from the spirit and scope of the invention, and the invention is thus not to be limited to the precise details of methodology or construction set forth above as such variations and modification are intended to be included within the scope of the invention.

What is claimed is:

1. A method of exfoliating, cleansing, hydrating, and soothing human facial skin having a normal combination skin type consisting the steps of:
   (i) providing the user with a beauty food kit consisting of
      (a) a dried particle mixture of dried flowers, dried herbs and/or dried foods in a sealed container, said container having a fill line printed on the container and said mixture consisting of:
         (i) *Avena sativa* kernel flour;
         (ii) *Zinigiber officinale* root extract;
         (iii) *Viola odorata* extract;
         (iv) kaolin; and
         (v) one of *Geranium thunbergii* extract, *Geranium maculatum* extract or *Ribes nigrum* fruit extract; and
      (b) a closed vial or sealed packet containing essential oil of *Vitis vinifera;*
   (ii) opening the sealed container and adding up to the level of the fill line a flowable food selected from the group consisting of water, milk, and yogurt;
   (iii) stirring the dried particle mixture and flowable food until uniform, thereby forming a facial treatment;
   (iv) adding the contents of the closed vial or sealed packet to the facial treatment mask; and
   (v) applying the facial treatment mask to normal, combination skin in need thereof.

2. A facial treatment mask prepared for a human user having normal combination skin, the facial treatment mask prepared by the steps consisting of:
   (i) providing a beauty food kit consisting of
      (a) a dried particle mixture of dried flowers, dried herbs and/or dried foods in a sealed container, said container having a fill line printed on the container and said mixture consisting of
         (i) *Avena sativa* kernel flour;
         (ii) *Zinigiber officinale* root extract;
         (iii) *Viola odorata* extract;
         (iv) kaolin; and
         (v) one of *Geranium thunbergii* extract, *Geranium maculatum* extract or *Ribes nigrum* fruit extract; and
      (b) a closed vial or sealed packet containing essential oil of *Vitis vinifera;*
   (ii) opening the sealed container and adding up to the level of the fill line a flowable food selected from the group consisting of water, milk, and yogurt;
   (iii) stirring the dried particle mixture and flowable food until uniform, thereby forming a facial treatment mask; and
   (iv) adding the contents of the closed vial or sealed packet to the facial treatment mask and mixing.

3. A method of exfoliating, cleansing, hydrating, and soothing human facial skin having a normal combination skin type consisting the steps of:
   (i) providing the user with a beauty food kit consisting of
      (a) a dried particle mixture of dried flowers, dried herbs and/or dried foods in a sealed container, said container having a fill line printed on the container and said mixture consisting:
         (i) *Avena sativa* kernel flour;
         (ii) *Zinigiber officinale* root extract;
         (iii) *Viola odorata* extract;
         (iv) kaolin;
         (v) one of *Geranium thunbergii* extract, *Geranium maculatum* extract or *Ribes nigrum* fruit extract; and
         (vi) powdered soy milk; and
      (b) a closed vial or sealed packet containing essential oil of *Vitis vinifera;*
   (ii) opening the sealed container and adding up to the level of the fill line a flowable food selected from the group consisting of water, milk, and yogurt;
   (iii) stirring the dried particle mixture and flowable food until uniform, thereby forming a facial treatment;
   (iv) adding the contents of the closed vial or sealed packet to the facial treatment mask; and (v). applying the facial treatment mask to normal, combination skin in need thereof.

4. A facial treatment mask prepared for a human user having normal combination skin, the facial treatment mask prepared by the steps consisting of:
- (i) providing a beauty food kit consisting of
  - (a) a dried particle mixture of dried flowers, dried herbs and/or dried foods in a sealed container, said container having a fill line printed on the container and said mixture consisting of
    - (i) *Avena sativa* kernel flour;
    - (ii) *Zinigiber officinale* root extract;
    - (iii) *Viola odorata* extract;
    - (iv) kaolin
    - (v) one of *Geranium thunbergii* extract, *Geranium maculatum* extract or *Ribes nigrum* fruit extract; and
    - (vi) powdered soy milk; and
  - (b) a closed vial or sealed packet containing essential oil of *Vitis vinifera;*
- (ii) opening the sealed container and adding up to the level of the fill line a flowable food selected from the group consisting of water, milk, and yogurt;
- (iii) stirring the dried particle mixture and flowable food until uniform, thereby forming a facial treatment mask; and
- (iv) adding the contents of the closed vial or sealed packet to the facial treatment mask and mixing.

\* \* \* \* \*